United States Patent [19]
Fleming et al.

[11] Patent Number: 6,090,593
[45] Date of Patent: Jul. 18, 2000

[54] ISOLATION OF EXPRESSED GENES IN MICROORGANISMS

[75] Inventors: James T. Fleming, Knoxville; Gary S. Sayler, Blaine, both of Tenn.

[73] Assignee: The United States of America as represented by the Secretary of the Air Force, Washington, D.C.

[21] Appl. No.: 09/078,283

[22] Filed: May 13, 1998

Related U.S. Application Data

[60] Provisional application No. 60/046,428, May 14, 1997.

[51] Int. Cl.$^7$ .............................. C12P 19/34; C12Q 1/68; C07H 21/04
[52] U.S. Cl. ........................... 435/91.2; 435/6; 435/91.1; 435/91.21; 536/23.1; 536/23.2; 536/23.7; 536/24.33
[58] Field of Search .............................. 435/6, 91.1, 91.2, 435/91.21; 436/23.1, 23.2, 23.7, 24.33

[56] References Cited

U.S. PATENT DOCUMENTS 5,665,547  9/1997  Pardee et al. ................................. 435/6

OTHER PUBLICATIONS

Kozak et al J. of Cell Bio vol. 115(4) pp. 887–903, 1991.
Palfner et al Onkologie vol. 18(suppl 2) pp. 369 abstract, 1995.
Stapleton et al Abstracts of 96th General meeting of ASM No. 96, 1996.
Simms et al Focus vol. 15 No. 4 pp. 99–102, 1993.
Fleming et al Applied and Env. Micro Oct. vol. 64 No. 10 pp. 3698–3706, 1998.
Gibco Catalog pp. 18–34, 1995.
Liang et al Curr. Opin. Immunol. vol. 7 pp. 274–280, 1995.
Jurecic et al Trends Genetic vol. 12 No. 12 pp. 502–504, 1996.
Fislage et al NAR vol. 25, No. 9 abstract, 1997.
Kwaik et al Mol. Micro. vol. 21 No. 3 abstract, 1996.
Yao et al (Abstracts Gen. Meeting ASM No. 97 p. 264, 1997.
Fleming, J.T., J. Sanseverino, and G.S. Sayler. 1993. Quantitative Relationship between naphthalene catabolic gene frequency and expression in prediction PAH degradation in solis at town gas manufacturing site. Environ. Sci. Technol. 27:1068–1074.
Fleming, J.T. and G.S. Sayler, 1995. Assessment of Gene Expression in the Environment: Quantitative mRNA Analysis in Contaminated Soils in R.A. Minear, A.M. Ford, L.L. Needham, N.J. Karch (ed.), Applications of Molecular Biology in Environmental Chemistry. Lewis Publishers, Boca Raton.
McClelland, M. and J.W. Welsh. 1994. RNA fingerprinting by arbitrarily primed PCR. PCR methods and applications.
McClelland, M., D. Ralph, R. CHeng and J. Welsh. 1994. Interactions among regulators of RNA abundance characterized using RNA fingerprinting by arbitrarily primed PCR. Nucl. Acid. Res. 22:4419–4431.
Neidhardt, C.F., J.C. Ingraham and M. Schaechter. 1990. Physiology of the bacterial cell, a molecular approach.
Wong, K.K. and M. McClelland. 1994 Stress–inducible gene of *Salmonella typhimurium* identified by arbitrarily primed PCR of RNA. Proc. Natl. Acid. Sci. 91:639–643.

*Primary Examiner*—Kenneth R. Horlick
*Assistant Examiner*—Jeffrey Siew
*Attorney, Agent, or Firm*—Thomas C. Stover

[57] ABSTRACT

The differential display (DD) technique, widely used previously for eukaryotic gene discovery, is optimized to detect differential mRNA transcription (an expressed gene) from both pure culture and soil derived bacterial RNA. A model system using toluene induction of TodC1 in *Pseudomonas putida* F1 is used to optimize the procedure. Once optimized, an arbitrary primer for the RT step in conjunction with the same arbitrary primer and a Shine-Dalgarno (SD) primer for the PCR reaction is used to detect the expressed gene. The invention thus provides a method for discovery and acquisition of novel genes from environmental microbial communities that avoids the traditional steps and inherent bias due to the culturing of environmental isolates.

7 Claims, 16 Drawing Sheets

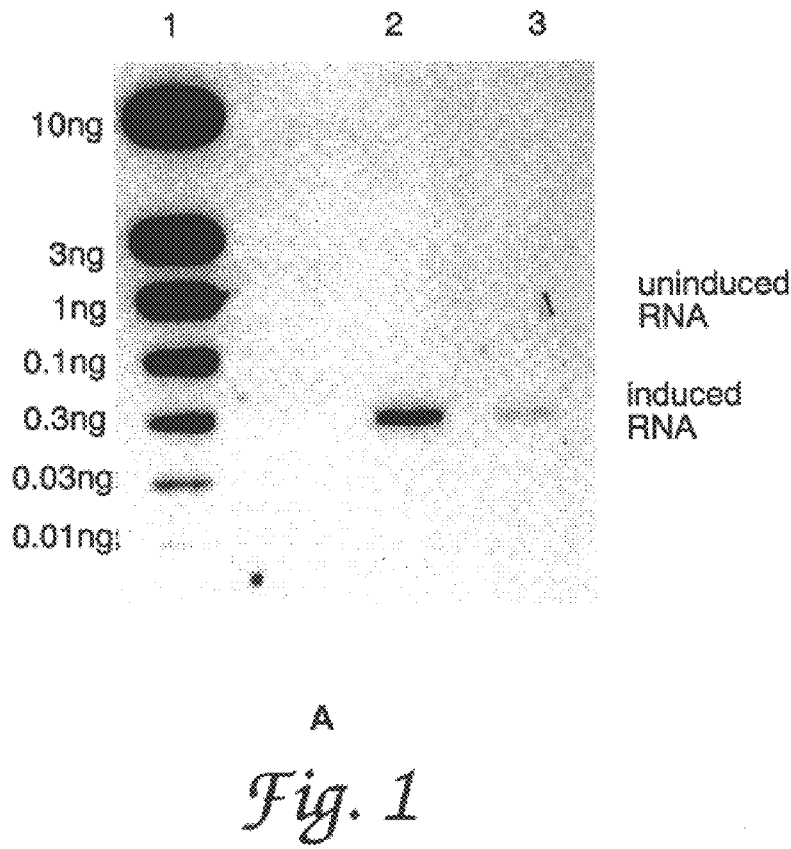

Figure 1. Quantitation of induced transcipts from pure cultures. (A) *P. putida* F1 cells grown in the presence or absence of toluene. Column 1; 10, 3, 1, 0.1, 0.03, 0.01 ng of *tod* DNA used as standards. Columns 2, 3; 10 µg of total RNA from induced total RNA from *P. putida* F1 was applied to the membrane in duplicate. A $^{32}$P- labeled *todC1* probe was used to hybridize with the blotted RNA. (B) *P. putida* JS150 cells grown in the presence or absence of salicylate. Column 1; 10, 3, 1, 0.1, 0.03, 0.01 ng of *nah* DNA used as standards. Columns 2, 3; 10 µg and 1µg, respectively, of total RNA from induced total RNA from *P. putida* JS 150 was applied to the membrane and probed with a $^{32}$P-labeled *nahA* fragment.

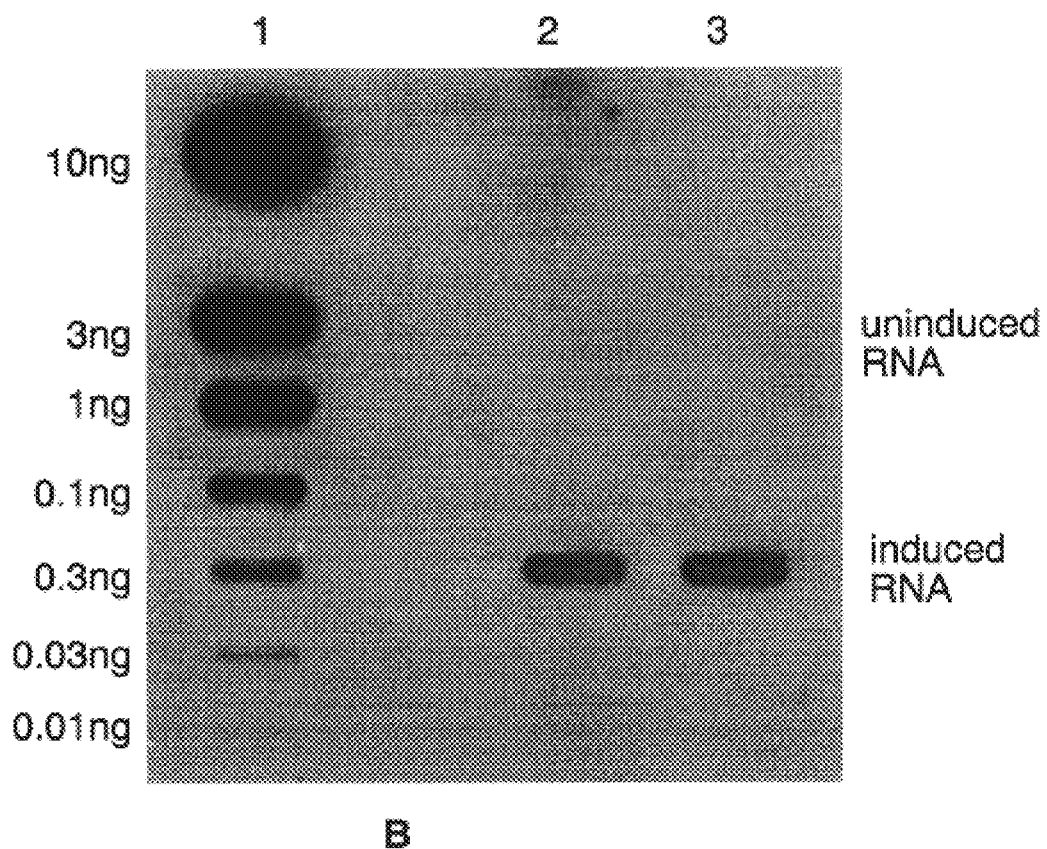
Fig. 1 (con't)

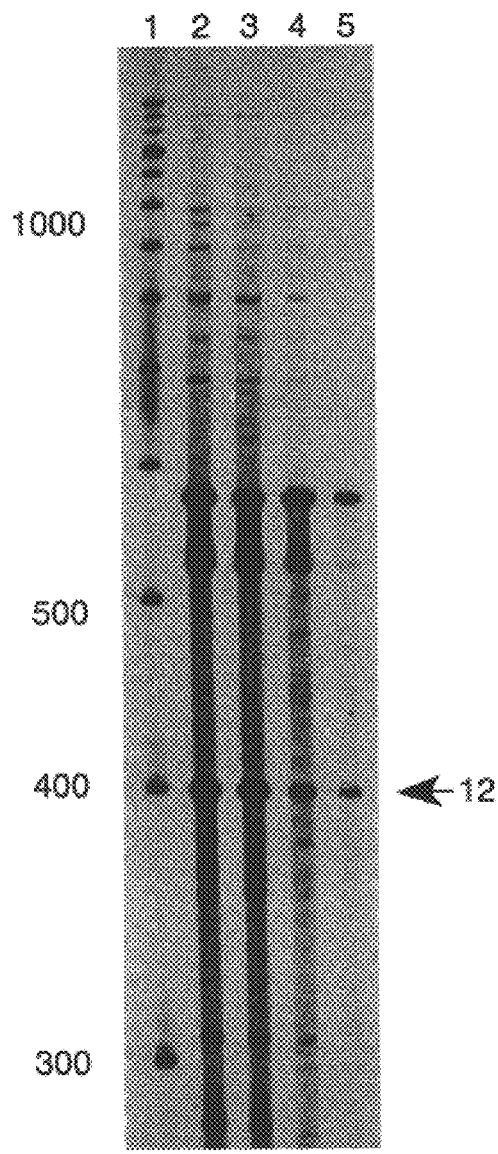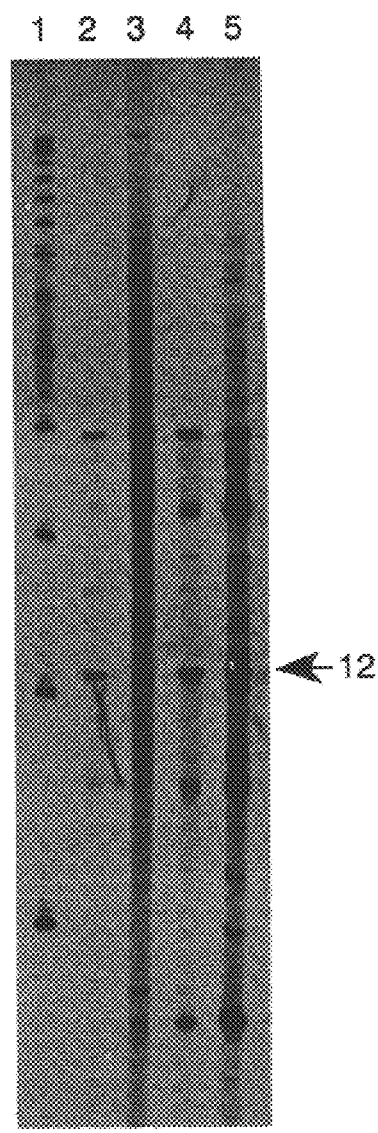

Figure 2. Determination RNA and MgCl$_2$ concentrations for differential display reactions. (A) Differing amounts of toluene induced RNA were used for differential display. Lane 1, 100 bp ladder; lane 2, 15 ng; lane 3, 1.5 ng; lane 4, 0.15 ng. (B) Effect of differing MgCl$_2$ concentrations on the complexity of banding pattern. Lane 1; 100 bp ladder; lane 2, 8 mM; lane 3, 4 mM; lane 4, 2 mM; lane 5, 1 mM. The *todC1* fragment is indicated by an arrow.

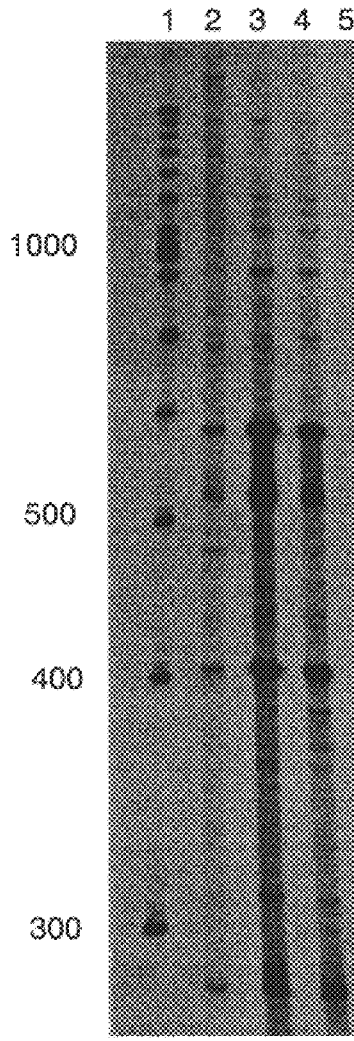 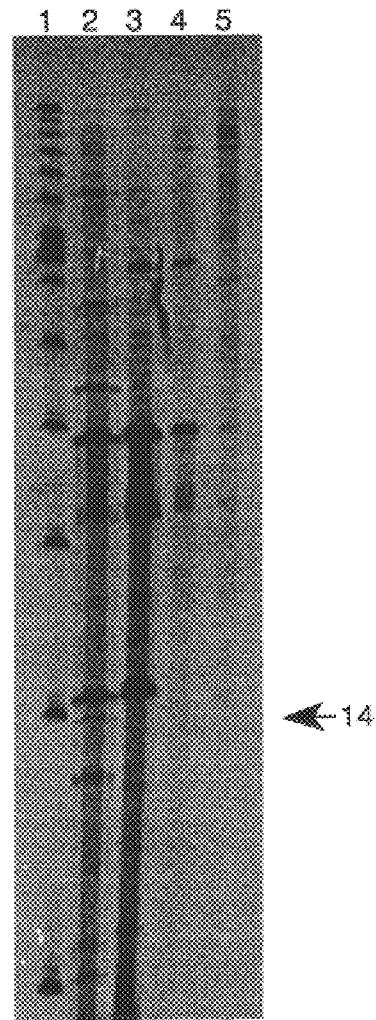

Figure 3. Optimization of nucleotide and primer concentration for differential display reactions. (A) Effect of varying nucleotide concentration on the complexity of banding patterns. Lane 1, 100 bp ladder; lane 2, 200 μM; lane 3, 20 μM, lane 4, 2 μM; lane 5, 0.2 μM. (B) Effect of varying primer concentration on the complexity of banding patterns. Lane 1, 100 bp ladder; lane 2, 2μM; lane 3, 0.2 μM; lane 4, 0.02 μM, lane 5, 0.002 μM. The todC1 fragment is indicated by an arrow.

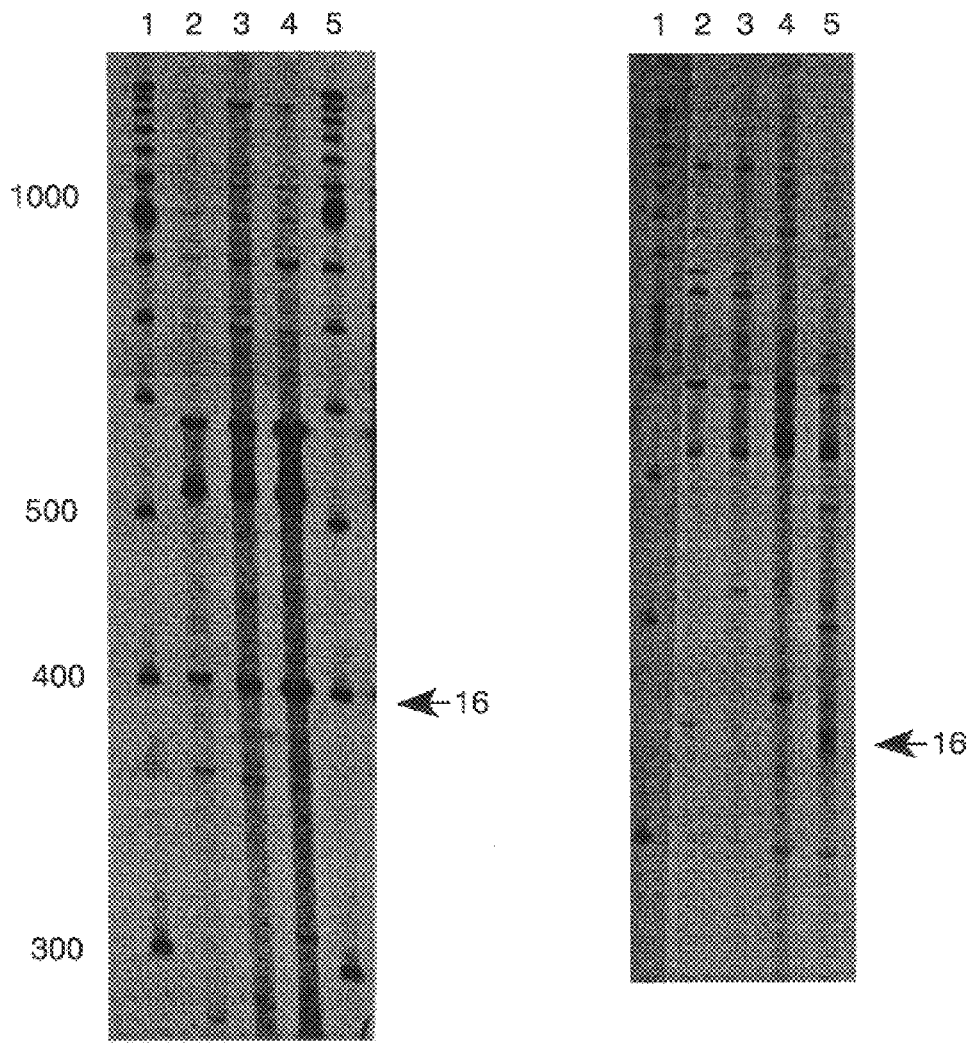

Figure 4. Optimization of annealing temperature and primer length for differential display reactions. (A) Effect of varying annealing temperature on complexity of banding patterns. Lane 1, 100 bp ladder; lane 2, 30°C; lane 3, 40°C; lane 4, 50°C. (B) Effect of varying primer length between 10 and 13 bp on complexity of banding pattern. Lanes 1, 3; uninduced RNA; lanes 2, 4; toluene induced RNA. Lanes 1, 2, 10 bp; lane 3, 4, 13 bp. The todC1 fragment is indicated by an arrow.

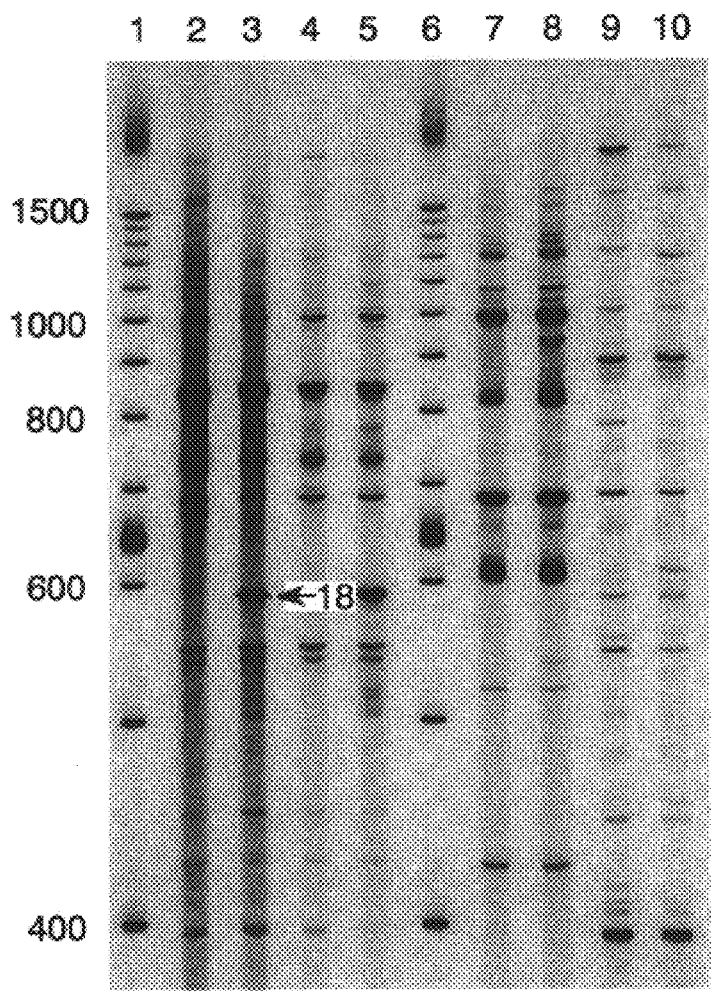
Figure 5. Differential display from uninduced and toluene induced *P. putida* F1 cells using arbitrary primers. Lanes 1, 6; 100 bp ladder. Lanes 2,4,7,9; uninduced. Lanes 3,5, 8,10; toluene induced. Primers used: 70.3 alone (lane7, 8) SD alone (lanes 9, 10) or both primers (lanes 1,2,3,4). The *todC1* fragment is indicated by an arrow.

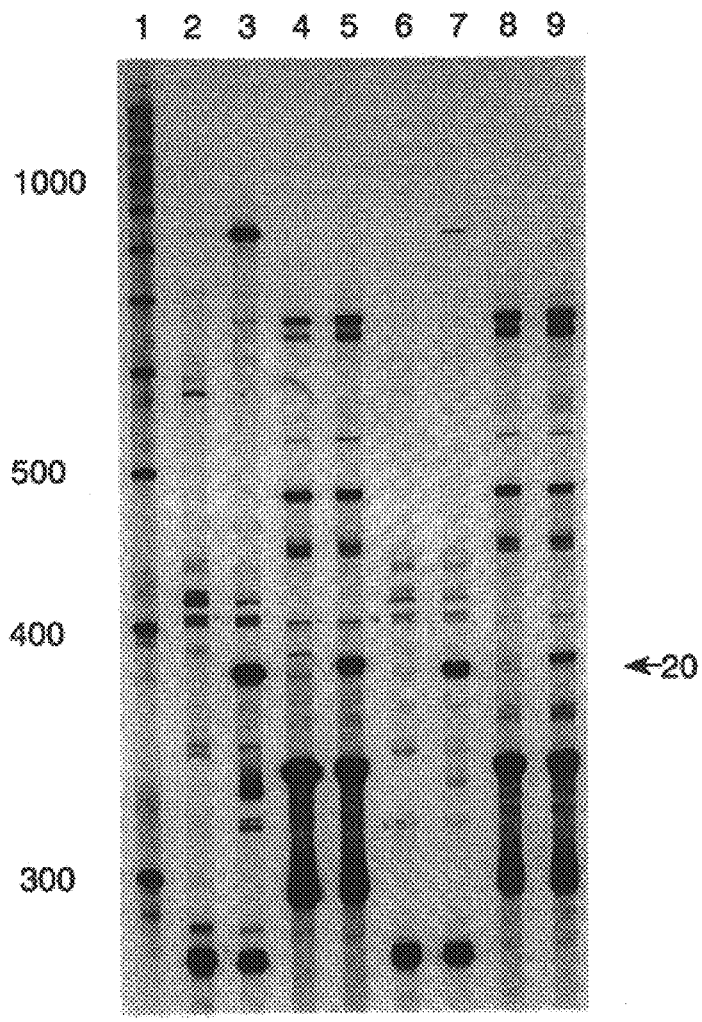

Figure 6. Differential display of salicylate induced and uninduced RNA from *P. putida* JS150 using arbitrary primers. Total RNA from uninduced and induced cells were reverse transcribed using a Shine-Dalgarno (SD14) primer followed by PCR using the SD14 primer and an arbitrary 10 bp primer. Lane 1, 100 bp ladder. Lanes 2, 3, 6, 7; PCR with primers SD14 and 60.3; lanes 3 and 7, induced; lanes 2 and 6 uninduced. Lanes 4, 5, 8, 9; PCR with primers SD13 and 60.4; lanes 5 and 9, induced; lanes 4 and 8, uninduced. The arrow points to the *nahA*-like fragment.

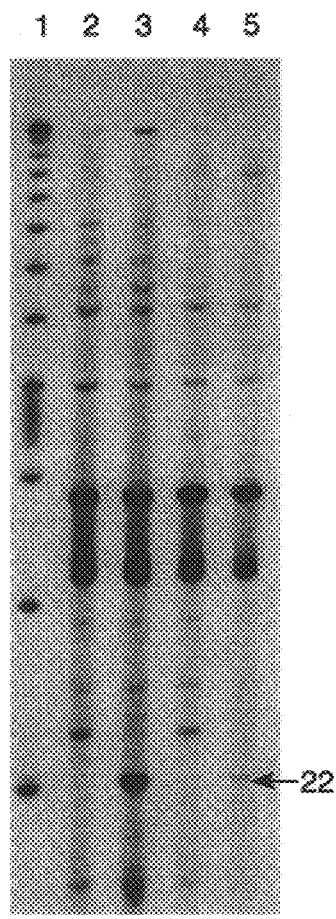

Figure 7. Differential display of toluene induced and uninduced RNA from *P. putida* F1 isolated from pure culture and soil samples. Lane 1, 100 bp ladder; lane 2, pure culture uninduced ; lane 3, pure culture toluene induced; lane 4, soil extracted uninduced; lane 5, soil extracted toluene induced. The arrow points to a band that, after cloning and sequencing, was revealed to be a *TodC1* fragment.

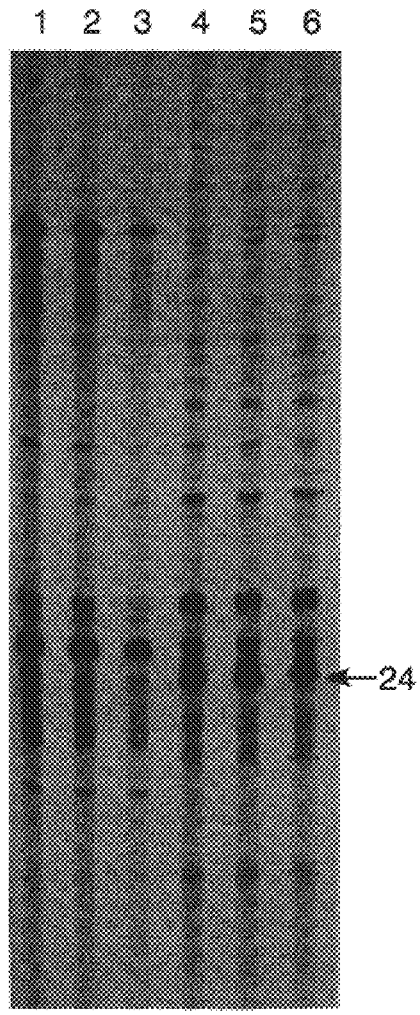

Fig. 8

Figure 8. Differential display of toluene induced and uninduced uninoculated soil microcosms. Total RNA from toluene induced and uninduced microcosms was reverse transcribed using the SD primer and amplified using the SD primer in conjunction with primer 70.3. Lanes 1,2,3: triplicate reactions from uninduced microcosms. Lanes 4, 5, 6: triplicate reactions from toluene induced microcoms. The arrow points to a band that was reamplifed, cloned, sequenced and verified as differentially expressed.

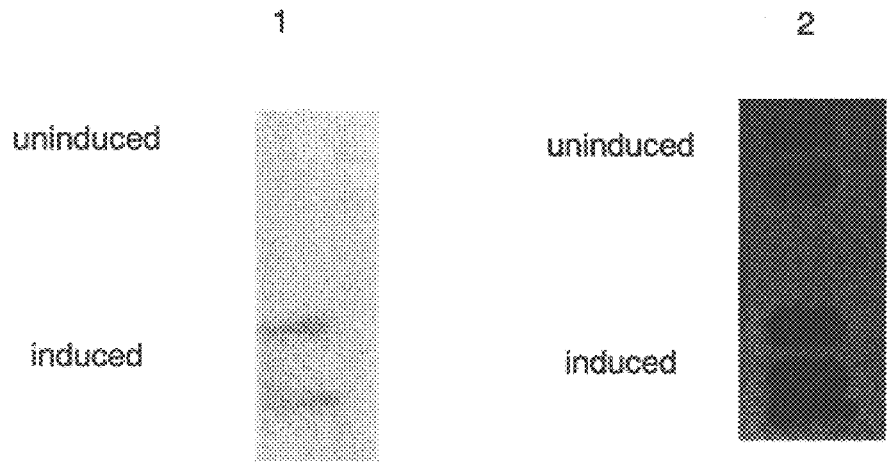

*Fig. 9A*

Figure 9. Confirmation of clonal differential expression by RNA slot blot analysis.

Total RNA was isolated from pure cultures or soil microcosms, blotted to nylon membranes and probed with $^{32}P$-labeled cloned fragments. (A) toluene induced and uninduced *P. putida* F1 RNA probed with inserts from clones 410 (1) and 170 (2). (B) Salicylate induced or uninduced *P. putida* JS150 RNA hybridized with clones 380 (1) and 325 (2). (C) Toluene induced or uninduced uninoculated soil microcosm RNA probed with labeled clones 400 (1) and 325 (2).

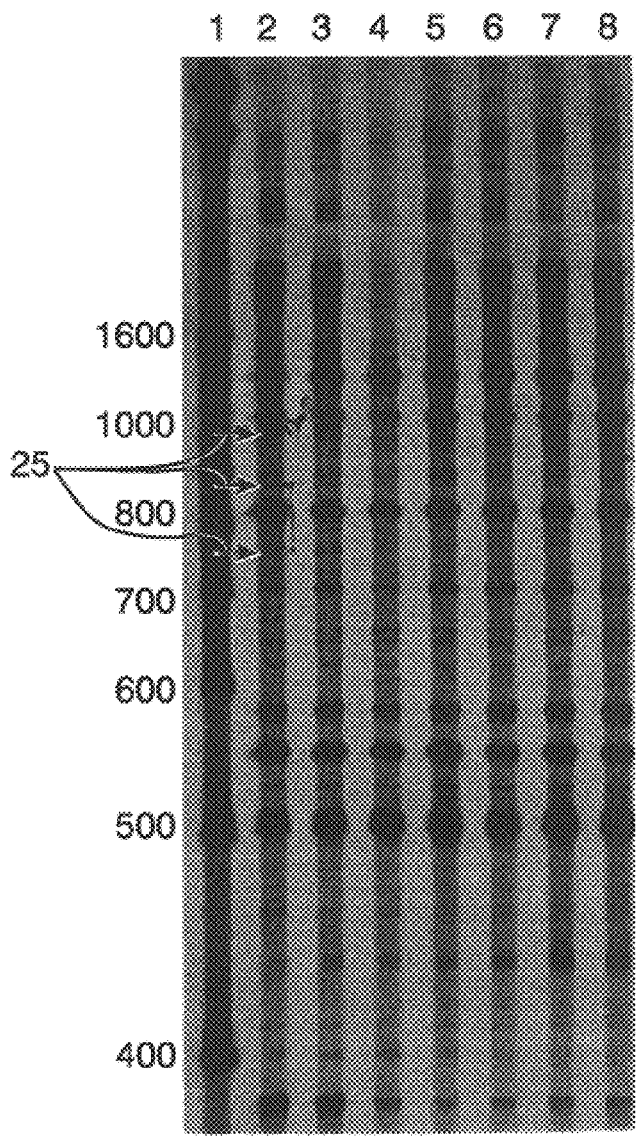
Figure 10. Differential Display of uranyl acetate induced *P. putida* G7 cells treated with rifampicin. Lane 1, 100 bp ladder; lane 2, T=0 min (without rifampicin); lane 3, T=5 min; lane 4, T=10 min; lane 5, T=20 min; lane 6, T=30 min; lane 7, T=40 min; lane 8, T=60 min.

Figure 11. Confirmation of uranyl acetate induction in P.putidaG7. A; Uninduced and uranyl acetate induced total RNA from P. putida G7 probed with clone 60.3-850. B; Uninduced and uranyl acetate induced total RNA from P.putidaG7 probed with clone 60.3-775.

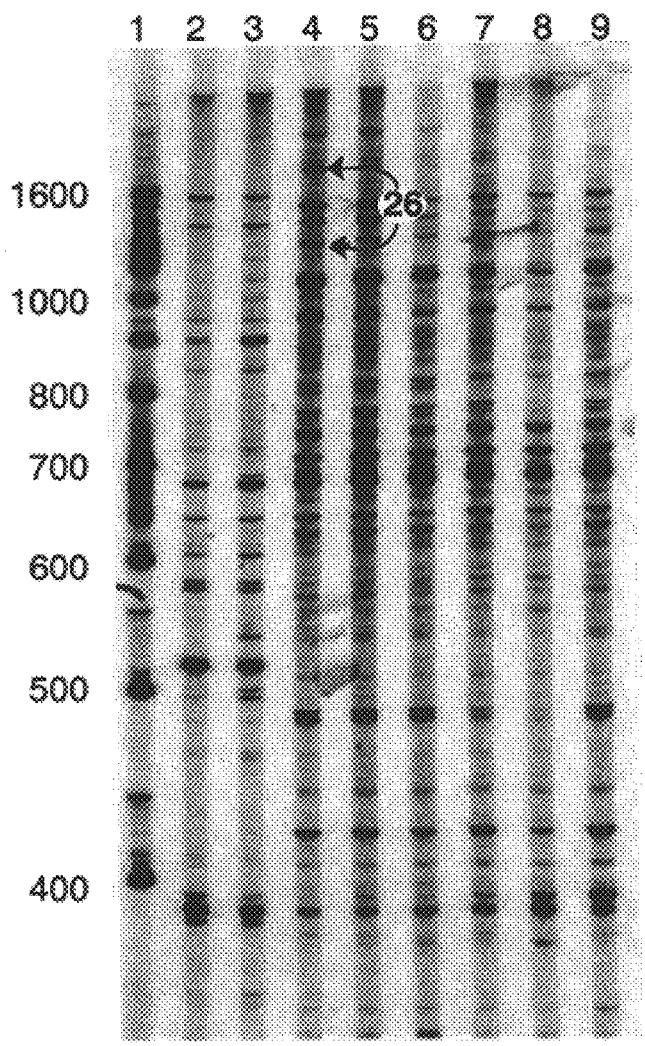

Fig. 12

Figure 12. Differential display of uranium induced and uninduced uninoculated soil microcosms treated with rifampicin. Total RNA was reverse transcribed using a 10 bp arbitrary primer followed by PCR with the same arbitrary primer and SD14 primer. Lane 1, 100 bp ladder; lanes 2, 3, duplicate control samples; lane 4, T=0 min (without rifampicin); lane 5, T=5 min; lane 6, T=10 min; lane 7, T=20 min; lane 8, T=40 min; lane 9, T=60 min. The arrows point to the bands that were isolated and reamplified.

Figure 13. Confirmation of uranyl nitrate induction of uninoculated soil microcosms. Lane 1, control microcosm total RNA; lane 2, $UO_2(NO_3)_2$ microcosm total RNA; lane 3, $Mg(NO_3)_2$ microcosm total RNA; lane 4, $Ca(NO_3)_2$ microcosm total RNA. Microcosm RNA was blotted to nylon membranes and probed with uranyl nitrate induced clone 60.3-1200.

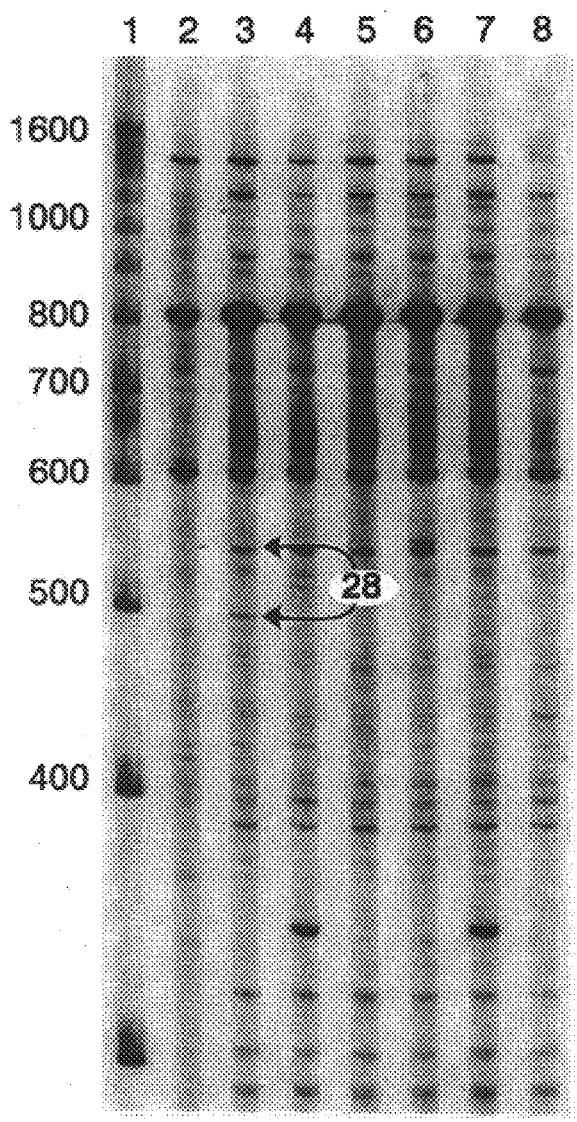
Figure 14. Differential display of cadmium induced *P. putida* G7. Lane 1, 100 bp ladder; lane 2, control total RNA; lane3, cadmium induced total RNA (T=0); total RNA from cadmium induced culture treated with rifampicin; lane 4, T=5 min; lane 5, T=10 min; lane 6, T=20 min; lane 7, T=40 min; lane 8, T=60 min. The arrows point to 2 putative differentially expressed bands.

ISOLATION OF EXPRESSED GENES IN MICROORGANISMS

CROSS-REFERENCE TO RELATED PATENT APPLICATIONS

This application claims domestic priority of a then copending provisional patent application, Ser. No. 60/046,428, having the same inventors, filed in the USPTO on May 14, 1997.

STATEMENT REGARDING FEDERALLY SPONSORED RESEARCH OR DEVELOPMENT

The invention described herein may be manufactured and used by or for the Government for governmental purposes without the payment of any royalty thereon.

BACKGROUND OF THE INVENTION

1. Field of the Invention

The present invention relates to identifying genes, particularly expressed genes in microorgansims.

2. Description of Related Art

There is often a need to identify expressed genes in soil particularly in contaminated soil so as to counter or reduce the effects of contaminates therein. Methods for the isolation and quantification of mRNA from environmental samples are designed to specifically measure in situ gene expression and activity. Direct extraction of mRNA from soil or soils and quantification of mRNA by ribonuclease protection assay has been demonstrated for naphthalene dioxygenase in soils and sMMO in aquifer sediments. Reverse transcriptase PCR amplification of mRNA for sMMO in activated sludge and lignin peroxidase in soils has also been demonstrated. These methods for mRNA analysis are a natural compliment to DNA extraction and hybridization or PCR analysis to detect gene sequences for catabolic genes or rDNA gene abundance in natural samples. In addition, direct mRNA analysis also provides potential evidence of in situ gene activity and conditions permissive of gene induction in the environment. These applications can be independent of microbial cultivation and hence, avoid many laboratory biases. However, these previous mRNA analytical methods are limited by the need for a priori information on gene sequences in order to design specific probes or primers for mRNA measurement. And there is a need to explore the use of differential display (DD) to quantify and recover novel mRNAs and/or cryptic or unknown DNA sequences transcribed under in situ conditions in soil.

For further information on DD see U.S. Pat. No. 5,665,547 to Pardee et al (1997) incorporated herein by reference.

While DD has very recently been applied to environmentally related research, the focus has been limited to eukaryotes. The technique has been used to discover genes induced in white-rot fungus by pentachlorophenol and rat Sertoli cells by cadmium acetate and polychlorinated biphenyls. In this regard, DD potentially allows identification of known or cryptic microbial genes that are differentially expressed under altered field conditions, such as chemical exposure, oxidative stress, extreme pH, anaerobiosis, heat shock, and starvation.

DD and the closely related RAP-PCR have been used to detect and isolate differentially expressed genes under induced and uninduced conditions in both eukaryotes and prokaryotes. The DD procedure, which uses a poly T primer for the RT reaction and an additional arbitrary primer for PCR has been exclusively applied to eukaryotic expression studies. RAP-PCR differs from DD in that arbitrary primers are used for both the RT and PCR steps, and as such, has been used for both eukaryotic and prokaryotic studies. For a further discussion of RAP-PCR see Welsh J. et al, *Arbitrarily Primed PCR Fingerprinting of RNA,* Nucleic Acids Res., Vol 20; 4965–4970, which is incorporated herein by reference.

Accordingly, there is need and market to detect and isolate differentially expressed genes under induced and uninduced conditions in microorganisms such as cultures including pure cultures and soil microcosms. And there has now been discovered such a method per the present invention.

BRIEF SUMMARY OF THE INVENTION

Broadly the present invention provides, a method for identifying at least one gene in a sample comprising, a) adding a contaminant to the sample to perturb microbial organisms in the sample and cause at least ore gene therein to be expressed, b) extracting RNA from the sample and c) isolating at least one type of expressed gene from the sample by differential display (DD).

In one embodiment, the inventive method isolates the gene by DD using an RT step and a PCR step in an inventive variation discussed below.

By "soil contaminant" as used herein is meant additives to the soil selected from the group of hydrocarbons, metals and a combination thereof in a form not naturally in the soil. The hydrocarbons can include, e.g., fuels, oils and toluene while the metals can include, e.g., cadmium and uranium.

BRIEF DESCRIPTION OF THE DRAWINGS

The invention will become more apparent from the following detailed specification and drawings in which, FIGS. 1, 9, 11 & 13 show RNA slot blots and FIGS. 2–8, 10, 12 & 14 show Differential Display gels. That is, FIG. 1 (A & B) demonstrates expression of tod and nah transcripts, respectively.

FIGS. 2 (A & B), 3 (A & B) and 4(A & B) are differential gels that demonstrate the progression of experiments that led to the optimization of the procedure.

FIGS. 5 and 6 demonstrate that differentially expressed gene fragments were obtained from using an arbitrary primer in conjunction with an SD primer, but not with arbitrary primers alone.

FIGS. 7 and 8 illustrate the differences between pure culture and soil-derived samples on differential display gels.

FIG. 9 (A, B & C) shows RNA slot blots verifying differential expression of several gene fragments obtained using the described differential display procedure.

FIG. 10 illustrates the use of the transcriptional inhibitor rifampicin to eliminate false positives on differential display gels;

FIG. 11 (A & B) is an RNA slot blot that verifies that the gene fragment so obtained is differentially expressed.

FIG. 12 demonstrates the acquisition of a uranium inducible gene from soil microcosms;

FIG. 13 demonstrates verification of differential expression of that gene fragment.

FIG. 14 demonstrates obtaining a cadmium inducible gene from pure culture.

DETAILED DESCRIPTION OF THE INVENTION

Figure 9B:
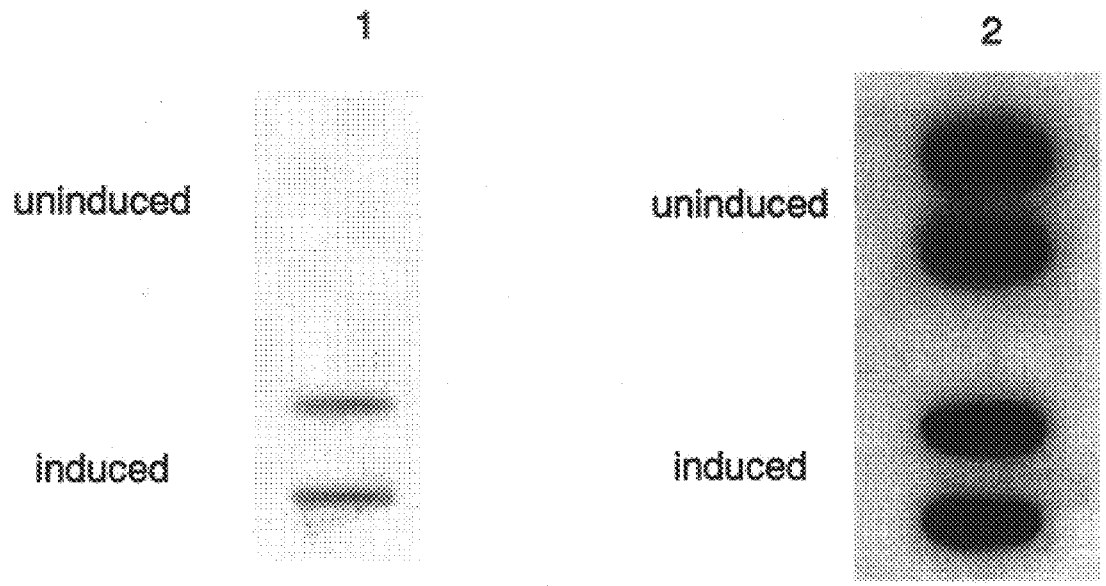

Referring in more detail to the invention a toluene degrading Pseudomonas putida F1 model system approach was chosen to optimize the DD procedure rather than a naphthalene induction system because toluene is believed more relevant to environmental concerns. Once the DD procedure was optimized and soil microcosm experiments became feasible, metals were chosen for induction experiments instead of complex organic mixtures because: 1) metal induction events are presumed to be simpler and thus less global in effect compared with organic chemical induction. 2) metals are commonly co-contaminants with organic chemicals at waste sites and present a difficult remediation challenge.

Subsequent to optimization, an arbitrary primer in conjunction with a primer for the SD region is used to detect toluene induced tod transcription in *P. putida* F1 and salicylate induction of a previously uncharacterized nahA positive transcript in *P. putida* JS 150. This approach is then applied to isolate several toluene, cadmium and uranium induced differentially expressed gene fragments from both inoculated and uninoculated soil microcosms.

In FIG. 2 a todC1 fragment is indicated by arrows 12.

In FIG. 3 a todC1 fragment is indicated by arrows 14.

In FIG. 4 a todC1 fragment is indicated by arrows 16.

In FIG. 5 a todC1 fragment is indicated by arrows 18.

In FIG. 6 a nahA-like fragment is indicated by arrow 20.

In FIG. 7 a todC1 fragment is indicated by arrow 22.

In FIG. 8 a differentially expressed band is indicated by arrow 24.

Figure 11:
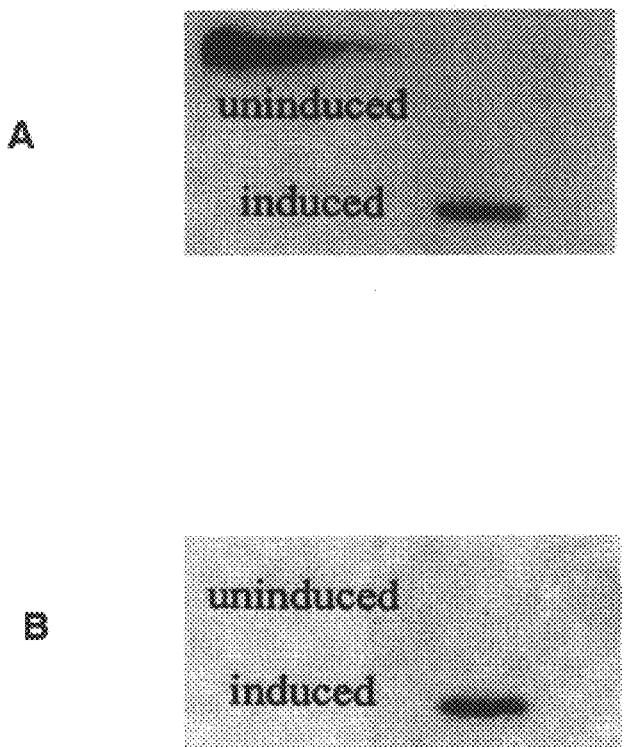

In FIG. 10 the arrows 25 point to three bands that were excised from gel, cloned and sequenced and two out of three were verified as differentially expressed (or induced) as shown in FIG. 11 hereof.

In FIG. 12 differentially expressed band are indicated by arrows 26.

In FIG. 14 differentially rxpressed bands are indicated by arrows 28.

The following examples are intended in illustration of the present invention and should not be construed in limitation thereof.

EXAMPLE 1

Cultivation of strains. A single colony of *Pseudomonas putida* F1 was used to inoculate 100 ml of YEPG media (1.0 g, dextrose; 2 g, polypeptone; 0.2 g, yeast extract; 0.2 g, $NH_4NO_3$/L, pH 7.0) in 250 ml flasks at 26° C. and shaken at 225 rpm overnight. One ml of the culture was collected and washed three times with phosphate buffered saline (PBS), (8.0 g, NaCl; 0.2 g, KCl; 1.15 g, $Na_2HPO_4$; 0.2 g, $KH_2PO_4$/L pH 7.0). The cells were resuspended in 100 ml of toluene saturated minimal salts media to induce tod gene expression under the same growth conditions. Similarly, colonies of *P. putida* JS150 (20) were used to inoculate YEPG for control cultures and YEPSS media (0.2 g, yeast extract, 2 g, peptone, 0.5 g, $NaC_7H_5O_3$, 2.7 g, $Na_2C_4H_4O_4$, 0.2 g $NH_4NO_3$/L, pH 7.0). This latter medium was used to induce nahA transcription. Minimal salts buffer (MSB) is composed of 4.0 g, $NaNO_3$; 1.5 g, $KH_2PO_4$; 0.005 g, $FeCl_3$; 0.2 g, $MgSO_4$; 0.01 g, $CaCl_2$; 0.5 g, $Na_2HPO_4$/L . *Pseudomonas putida* G7 was grown overnight at 30° C. in YEPG.

Primer synthesis. All primers were synthesized in-house using a DNA synthesizer Purification of full-length primers was done with reverse phase (RP) cartridges according to the manufacturer's protocol. The sequences of the TodC1 primers used were: tod13a (GTGCTCGACCATG) (antisense) and tod13s (CACATGCTCGACC) (sense) or tod10a (GTGCTCGACC) (anti-sense) and tod10s (CACATGCTCG) (sense). These primers amplify a 384 bp fragment from the TodC1 gene of strain *P. putida* F1. TodC1 primers tod20a (ATGAATCAGACCGACACATC) (antisense) and tod30s (AGACGGTCATGTGCTCGACCACTAGTTTCG) (sense) amplify a 940 bp fragment from *P. putida* F1 DNA. The sequences for the arbitrary 10 bp primers used were obtained from a commercial arbitrary primer set (Genosys Biotechnologies, The Woodlands, Tex.) and their designations are as follows: 60. 1, (CGCAGTACTC); 60.2, (GTCCTACTCG); 60.3, (CGAAGCGATC); 60.4, (GTCCTTAGCG); 60.5, (GTCCTCAACG); 60.8, (GTCCTCAGTG)); 70.3, (ACGGTGCCTG); 80.3, (CCATGGCGCC); 80.7, (GCACGCCGGA). The Shine-Dalgarno primer SD14 (GGGGAACGACGATG) was derived from a comparison of several bacterial mRNA start sites. The sequence of nah specific primers were: nahA3, (CCTTAGCGCGTAACTACCCC) and nahA 4, (GGTCCAGACCTTGGTGGTG). These two primers flank bases 2262 to 3291 of the NAH7 plasmid allowing amplification of a 1030-bp fragment.

EXAMPLE 2

RNA extraction from pure culture. RNA extraction was done using two methods: RNeasy columns and a modified hot phenol procedure. Small-scale extraction of RNA from RNeasy columns was the preferable source for RNA fingerprinting. Large-scale extraction of RNA by the hot phenol method was the source of RNA for RNA slot blots. The procedures for RNA extraction with RNeasy columns were followed according to manufacturer's protocol. Total mRNA from large scale-preps was done by the hot phenol method. 50 ml of mid log phase ($OD^{600}=0.6$) cells were collected by centrifugation at 1,935×g (4,000 rpm, JA-20 rotor, Beckman) for 15 minutes in 50 ml disposable centrifuge tubes. The cells were then resuspended in 20 ml of 0.05 M $NaC_2H_3O_2$, 1% $Cl_2H_{25}NaO_4S$ (SDS) buffer (pH 5.2) at 60° C. and 20 ml of phenol/chloroform (1:1) was added to the solution. The tubes were shaken by hand briefly and kept at 60° C. for 5 minutes after which the tubes were shaken with the wrist action shaker for 5 minutes. The tubes were cooled on ice for 2 minutes and were then centrifuged at 1,935×g for 15 min using a Beckman table-top centrifuge. The supernatant was transferred to a fresh tube and re-extracted three times. The final supernatant was removed to a baked 150 Corex bottle and 0.1 volume 3 M $NaC_2H_3O_2$ and 2.5 volumes of ice-cold ethanol was added to the solution. The solution was allowed to sit at −80° C. for 15 minutes and centrifuged at 12,096×g (10,000 rpm, JA-20 rotor, Beckman) for 30 minutes at 4° C. The pellets were resuspended in 500 μl of $C_6H_{10}O_5$ (DEPC) treated water, 2 μl of RNase free/DNase I (30 U/μl and 50 μl of Mg/DTT (100 mM) was added and allowed to incubate at 37° C. for 30 minutes. The RNA solution was then extracted with the same phenol/chloroform (1:1) solution three times and again precipitated by the addition of 0.1 volume of 3M NaC2H302 and 2.5 volumes of ice-cold ethanol. The RNA pellet was then washed twice with ice cold 70% ethanol, dissolved in 100 μl DEPC water and quantified by using UV spectroscopy (Beckman, Fullerton, Calif. model DU-70).

RNA integrity determination RNA integrity was verified with Northern gels (36). 10 μg of total RNA was incubated with 10 μl of formamide, 3.5 μl of formaldehyde and 2 μl of 5X MOPS buffer (0.1 M $C_7H_{15}NO_4S$, pH 7.0, 40 mM $NaC_2H_3O_2$ and 5 mM $C_{10}H_{16}N_2O_8$ (EDTA), pH 8.0) in a volume of 20 μl at 65° C. for 15 minutes. The RNA was then electrophoresed on 1.2% denaturing gels containing 18% formaldehyde along with 2 μl of loading dye and 1 μl of ethidium bromide (10 mg/ml). RNA was judged to be intact if the 16S and 23S rRNA subunits were visually well-defined bands after electrophoresis.

EXAMPLE 3

Uranium Induction in pure culture. Following overnight incubation, a 20ml aliquot of pure culture PpG7 was transferred to 80ml of fresh YEPG media in the presence of 200 μM uranyl acetate. Since previous literature suggests that uranium uptake occurs at a fairly rapid rate, cells were harvested following a 30 min incubation.

Cadmium Induction in pure culture. After overnight incubation a 5 ml aliquot of pure culture derived PpG7 was transferred to 95 ml of fresh YEPG media in the presence of 100 μM cadmium chloride. Cells were harvested in early log phase.

EXAMPLE 4

Soil Microcosms.

Toluene Induction (per the invention). Soil aquifer samples were obtained from bore-holes in an acquifer in Columbus, Miss. that had been stored at 4° C. for 1 year. In initial experiments, flasks containing 10 g of soil in 20 ml water were inoculated with P. putida F1 at $10^8$ cells/g soil and incubated at 26° C. with shaking at 225 rpm overnight. To induce cells, toluene was added in the saturated vapor phase. Subsequently uninoculated microcosms were prepared using the same aquifer soil. 10 g soil was incubated in 25% YEPG for 4 h in shake flasks with and without toluene. After 4 h slurry samples were simultaneously processed for total RNA and enumeration of culturable organisms as described as described in an Article by J. T. Flemming et al in *Quantitative Relationships . . .* (1993) *Envir. Sci. Technol.,* 27:1068–1074, which is incorporated herein by reference. Colony hybridizations were also performed using the enumerated plates for colony lifts, as described in such Article, and probed with a PCR generated TodC1 fragment.

RNA extraction from Soil Microcosms. 10 ml of soil slurry was added to a extraction solution consisting of 5 ml of extraction buffer (100 mM $C_4H_{11}NO_3.HCl$ (Tris) 1.4 M NaCl, 20 mM EDTA, 1% SDS), 5 ml phenol, pH 8.0 (equilibrated with Tris) and 5 ml chloroform pre-warmed to 60° C. The soil solution, in baked 25 ml Corex centrifuge tubes, was incubated at 60° C. for 5 min then shaken by mechanical action on a wrist action shaker for 5 min. The tubes were then centrifuged for 15 min at 12,096×g at 4° C. and the supernatants were extracted again with 10 ml chloroform. 5 μl of linear acrylamide was added as a co-precipitant, 15 ml of isopropanol was added and the tubes were stored overnight at −20° C. The following day the tubes were centrifuged at 12,096×g for 15 min and the pellet was resuspended in 200 μl DEPC treated water. The soil derived RNA solution was then DNase treated, phenol/chloroform extracted and ethanol precipitated. The concentration of soil extracted total RNA was estimated on the basis of absorbance at 260 and 280 nm.

A PCR constructed NahA template linked to a T7 promoter was used to transcribe a labeled NahA RNA probe according to manufacturer's protocols. After precipitation, the RNA probe was dissolved in 100 μl of DEPC treated water and 1 μl of the RNA was counted by scintillation countng. 160,000 cpm of the labeled RNA solution was added to the soil sample as an internal standard to estimate the RNA recovery rate.

EXAMPLE 5

Uranium Induction (per the invention). Soil microcosms consisted of 20 grams of an aquifer soil in the presence of 80ml of quarter-strength YEPG media. Microcosms were incubated for 24 h at 30° C. prior to uranium exposure Following the 24 h incubation period, 200 μM uranyl nitrate was added to the appropriate microcosm. Following a 30 m-in exposure to uranium, a 10 ml aliquot of the soil slurry was taken from each microcosm (Control and induced) for RNA extraction. To ensure that induction was due to uranium and not nitrate two additional controls were used: a soil microcosm containing 200μM calcium nitrate and a soil microcosm containing 200μM magnesium nitrate. These two compounds were chosen on the basis that each had an appropriate molecular weight in comparison to uranyl nitrate.

EXAMPLE 6

Preparation of radiolabled gene probes. Gene probes were prepared by random primer extension or by PCR. For the random primer method, the template DNA was restricted, electrophoresed in agarose gels, excised, and placed into a pre-weighed tube. 3 ml of distilled water/g of gel was added to the tube and heated at 65° C. for 5 minutes to melt the gel. 21 μl of the resulting DNA solution was used to prepare for the probe according to manufacturer's protocols. PCR generated double stranded probes were produced by substituting $\alpha$-$^{32}$P-dCTP(600 Ci/mmol) for cold dCTP in the standard PCR reaction. After PCR amplification, probes were denatured by boiling for 10 min prior to being added to prehybridized filters.

EXAMPLE 7

Time-course analysis of tod gene induction. A single colony of P. putida F1 was used to inoculate 50 ml of YEPG broth in a 250 flask which was incubated overnight at 26° C. on a rotary shaker at 225 rpm. The culture was harvested by centrifugation, washed three times with PBS buffer and resuspended in 500 ml of MSB medium saturated with toluene vapor and incubated at 26° C. on a rotary shaker at 225 rpm. 50 ml of the resuspended culture was taken at 0, 1, 3, 6, 9 and 24 hr intervals. The cells were collected by centrifugation at 1,935×g. RNA was isolated using RNeasy columns. 5 μg of each RNA sample was dissolved in a solution of 50% deionized formamide, 7% formaldehyde, 1×SSC (0.15M NaCl, 0.015M $Na_3C_6H_5O_7$) in a total volume of 40 μl, incubated at 68° C. for 15 min and cooled on ice. 2 volumes of 20×SSC (3M NaCl, 0.3 M $Na_3C_6H_5O_7$) was then added to each sample and the resulting solution was slot blotted to nylon membranes. The membranes were dried at 25° C., baked at 80° C. for 2 h and hybridized with a PCR generated TodC1 probe.

Quantitative assays for tod and nah mRNA induction P. putida F1 cultures were grown overnight with shaking at 26° C.; uninduced cells were grown in 50 ml of YEPG medium and induced cells were grown in 50 ml of MSB medium in 250 flasks with toluene vapor. Cells were harvested at mid-log phase ($OD^{600}$~0.6), RNA was isolated with RNeasy columns and slot-blotted to nylon membranes as described above. 10, 3, 1, 0.3, 0.1, 0.03 and 0.01 ng of TodC1 DNA was also blotted on the same membrane as standards. The membrane was hybridized with a TodC1 $^{32}$P-labeled probe, washed, applied to film and quantitation of transcripts was accomplished using a photo-imager. Similarly *P. putida* JS150 was grown in 50 ml of YEPSS medium, the total RNA was extracted and blotted to nylon membranes along with nahA DNA standards. The blots were processed as described above and probed with a $^{32}$P-labeled nahA probe.

Quantitation of tod and nah transcription. Toluene induced tod gene expression in *P. putida* F1 was induced after 3 h and reached maximal induction at 24 h (data not shown). Tod transcripts were undetectable in the uninduced sample. In a comparison with known amounts of tod DNA, the amount of tod transcripts was determined to be 0.04 ng or $7.8 \times 10^7$ transcripts /μg of total RNA (FIG. 1A). In a comparison with known amounts of nahA DNA, the amount of nahA-like transcripts was determined to be 0.05 ng or $9.7 \times 10_7$ transcripts /μg of total RNA (FIG. 1B).

EXAMPLE 8

RNA-DNA Hybridization. Hybridization was done according to the method of Church and Gilbert. Membranes were incubated in prehybridization solution (0.5 M $Na_2HPO_4$, 1 mM EDTA, 7% SDS, pH 7.3) for 4 h at 65° C. in a shaking water bath. $^{32}$p-labeled probe was added to the prehybridization solution and incubated overnight at the same temperature. The membranes were washed four times with high stringency wash buffer (1.17 g, NaCl; 6.3 g, Tris-HCl; 0.74 g, EDTA; 10 g, SDS/2 litter, pH 7.3). Blots were placed in plastic bags, laid on x-ray film at −80° C. with intensifying screens and developed after 18–48 hrs.

EXAMPLE 9

Optimization of differential display using tod specific primers (per the invention). Using toluene induced *P. putida* F1 RNA as a model system, several parameters were varied in parallel using a set of specific tod primers to allow optimization of the differential display reaction conditions: I) template concentration: 15, 1.5 , 0.15 and 0.015 ng. II) Magnesium concentration: 8, 4, 2, and 1 mM. III) primer concentration: 2, 0.2, 0.02, and 0.002 μM. IV) annealing temperature: 50, 40, and 30° C. V) dNTP concentrations: 200, 20, 2, and 0.2 μM. VI) primer lengths: 10 and 13 bp. The invariant parameters for all other components were maintained at the concentrations described in the next two paragraphs.

Complimentary DNA was synthesized by Moloney murine leukemia virus (MMLV) reverse transcriptase (RT) (BRL). A todC1 antisense 10 bp or 13 bp primer was first used for initial optimization and, subsequently, arbitrary 10 bp primers were used. The final concentration of components was: dNTPs, 200 μM; dithiothreitol, 5 mM; MMLV enzyme, 50 U; total RNA, 200 ng; primer 0.4 μM; 1 X MtLV reaction buffer (BRL) in a total reaction volume of 20 μl. The RT reaction was carried out in a thermal cycler using the following program: ramp 50° C. to 30° C. for 15 min; 37° C. for 1 h; 95° C. for 5 min; followed by an incubation at 4° C.

The PCR step was performed with a thermal cycler incorporating $^{32}$P or $^{33}$P labeled nucleotides for visualization by autoradiography. The final concentrations of components in the 27 (1 reaction were: Taq polymerase (BRL), 0.3 U; dNTPs 20 μM; dimethylsulfoxide, 6%; primer, 2 μM; labeled nucleotide 0.25 μl; 10% triton, 0.1%; 1×PCR reaction buffer in 27μl. Following addition of 3 μl of the RT reaction, the solution was cycled at 94° C. for 30 s (denaturing), 40° C. for 2 min (annealing), and 72° C. for 1 min or 94° C. for 15 sec; 40° C. for 30 s; and 72° C. for 60 s. 40 amplification cycles were used for both machines followed by a 10 min final extension at 72° C.

The PCR products were run on 340 μm×61cm×33 cm, 4.5% denaturing acrylamide gels in side-by-side fashion. 4 μl of the RT-PCR reactions were loaded onto the sequencing gel along with 4 μl of denaturing loading dye (95% formamide, 20 mM EDTA, 0.05% bromophenol blue, 0.05% xylene cyanol FF) after boiling at a water bath for two min. The gel was run on a sequencing apparatus for 2 hours at 2,700V. The gel was then dried directly on the glass by three cycles of sequential washing (2 min) in water and drying (15 min) to dissolve the urea. The dried gel was then exposed to to X-ray film at room temperature for 18–48 hrs.

Optimizing prokaryotic differential display using specific primers

Optimization conditions. For the electrophoretic gel protocol described using the Genomyx LR, the average number of amplification products represented by visible bands were 70 per lane with lengths ranging from 100 bp to 2 Kbp. After initial optimization, electrophoresis of the DD-PCR products from *P. putida* F1 RNA was successful, resulting in a TodC1 fragment of the expected size only detected in induced samples. When a series of decreasing RNA template concentrations were used, the TodC1 fragment could still be detected when the total RNA was lowered to 0.015 ng with only a slight decrease in intensity (FIG. 2A). The lower template concentration also decreased the background. When a primer concentration of 0.2 (M was used, the optimal magnesium concentration was between 1 to 1.5 mM (FIG. 2B). The effect of changing dNTP concentration was considerable (FIG. 3A). Above 1 mM, the band number and intensity dramatically decreased. The optimal primer concentration was found to range from 0.2 μM to 2 μM. Above 20 μM, mis-priming was greatly increased. When the primer concentration was lower than 0.02 μM, band intensity also dramatically decreased (FIG. 3B). Only a slight change in band pattern was observed when the annealing temperature was increased from 30 to 50° C. (FIG. 4A). The primer length also had a great influence on fingerprinting band patterns (FIG. 4B); more bands per lane were obtained by using longer primers.

EXAMPLE 10

Differential display from pure cultures using arbitrary primers (per the invention).

Toluene induction. After optimization with specific primers, an attempt was made to detect tod transcription using arbitrary primers alone or in conjunction with the SD14 primer. Primers 70.3, 80.2 and 80.5 were randomly selected and DD was performed using the same *P. putida* toluene induced RNA under the same conditions as used with the tod specific primers.

Salicylate induction

Salicylate induced and uninduced *P. putida* JS150 RNA was used for a series of reactions using arbitrary primers 60.1, 60.5, 60.3, 60.4, 60.8 and 80.7 separately for the RT reaction and primer SD14 in conjunction with the same arbitrary primer for PCR.

Uranyl acetate induction. Uranyl acetate induced *P. putida* G7 was used for DD using arbitrary primers 60.3 for the RT reaction and primer SD 14 in conjunction with the same arbitary primer for PCR.

Cadmium chloride induction. Cadmium chloride induced *P. putida* G7 was used for DD using arbitrary primers 70.3 for the RT reaction and primer SD14 in conjunction with the same arbitrary primer for PCR.

Differential display of pure culture derived RNA using arbitrary primers

Toluene induction and verification. Compared to the RNA fingerprints generated using specific primers, more bands per lane were observed when single arbitrary primers were used (data not shown). From several differential bands detected on the DD gel (FIG. 5), one of the bands from the 70.3 lane was verified to be differentially expressed using the reamplified PCR product to probe RNA slot blots. Sequence analysis revealed both of these two differentially expressed PCR fragments to be overlapping but nonidentical toluene dioxygenase fragments 5' to the 380 bp fragment amplified using the tod specific primers.

Salicylate induction and verification The RNA fingerprints from salicylate induced and uninduced *P. putida* JS 150 cells did not result in differential bands when primers 60.1, 60.5, 60.8 and 80.7 were used, but primers 60.3 and 60.4 yielded several differential bands (FIG. 6). Cloning and sequencing of the reamplified clone 60.3–380 revealed it to have 90% homology with a Psuedomonas reductase (ntdAc) gene and 81% homology with the naphthalene dioxygenase (nahAc) gene. Clone 60.3–380 was verified to be differentially expressed on the basis of RNA slot blots (FIG. 9B- 1). Probing slot blots with clone 60.3–325 revealed it to be a ribosomal subunit and allowed it to serve as an indicator of equal slot blot loading (FIG. 9B-2). The sequence of clone 60.3–380 was submitted to GenBank and was given the accession number AF00 1828.

Uranyl acetate induction and verification. Because it is difficult at times to distinguish authentic hits from the differential display, the use of the bacterial transcriptional inhibitor, rifampicin, allowed us to further delineate between 'true' mRNAs responsible for induction and other artifacts (such as rRNAs and tRNAs) which are a commonplace to the differential display. Since rifampicin specifically binds to the β subunit of the bacterial RNA polymerase preventing further transcription initiation, one should see on the differential display gel a gradual decrease of the message which had been induced in the presence of uranyl acetate. RNA fingerprints generated by differential display resulted in 3 putative differentially expressed bands (FIG. 10). Following reamplification by PCR, PCR products were resolved on a 1% low-melting agarose gel to confirm the correct fragment had been isolated (data not shown). Each of the three cDNAs were cloned, sequenced, and compared to other sequences on the GenBank Blast algorithm. Results from sequence analysis revealed that two out of the three sequences had the potential to be novel. Clone 60.3–850 had the closest similarity (67%) to the Escherichia coli RNA polymerase alpha subunit. Clone 60.3–750 had the closest similarity (67%) to the Psedomonas putida trpA and trpB genes for tryptophan synthase. Clone 60.3–1000 showed the most homology of any of the 3 sequences presented to the sequence database. Over a 370 base sequence from clone 60.3–1000 matched almost perfectly (98%) to the rpoB gene of Pseudomonas putida which encodes for the RNA polymerase β subunit (2, 26). Based on this result it was assumed that the sequence obtained for clone 60.3–1000) was not novel. Verification of differential expression was done using total RNA obtained from control versus induced cultures and slot blotted onto a nitrocellulose membrane. Results from slot blot analysis revealed that each of the three bands obtained from the differential display gel were confirmed to be differentially expressed (FIG. 11). This further establishes the use of rifampicin to discriminate between false positives and authentic differentially expressed transcripts from the gel.

Cadmium chloride induction. The results for the cadmium induction experiment were similar to those obtained with uranyl acetate. One putative differentially expressed band of 500 bp was obtained using the 70.3 primer(FIG. 14).

EXAMPLE 11

Differential display of un inoculated soil microcosm RNA (per the Invention).

Toluene induction Toluene induced and uninduced RNA extracted from uninoculated soil microcosms was used for differential display using primer 70.3 for the RT reaction and primer SD14 in conjunction with primer 70.3 for PCR. The conditions used for both the RT and PCR steps were identical to those described above with the exception that the amount of microcosm total RNA used for the RT reaction was 100 ng.

Uranium nitrate induction. Uranyl nitrate induced soil microcosm RNA was used for DD using arbitrary primers 60.3, 60.5 and 60.1 for the RT reaction and primer SD 14 in conjunction with the same arbitary primers for PCR.

Differential display of toluene induced soil microcosm derived RNA

Inoculated microcosms. The RNA fingerprints from pure culture and inoculated soil microcosms were virtually identical (FIG. 7). However, the TodC1 band was fainter in the soil sample versus the pure culture sample (FIG. 7). Recovery rates of $^{32}$P-labeled RNA were approximately 75% from this soil using the protocol as described.

Figure 9C:
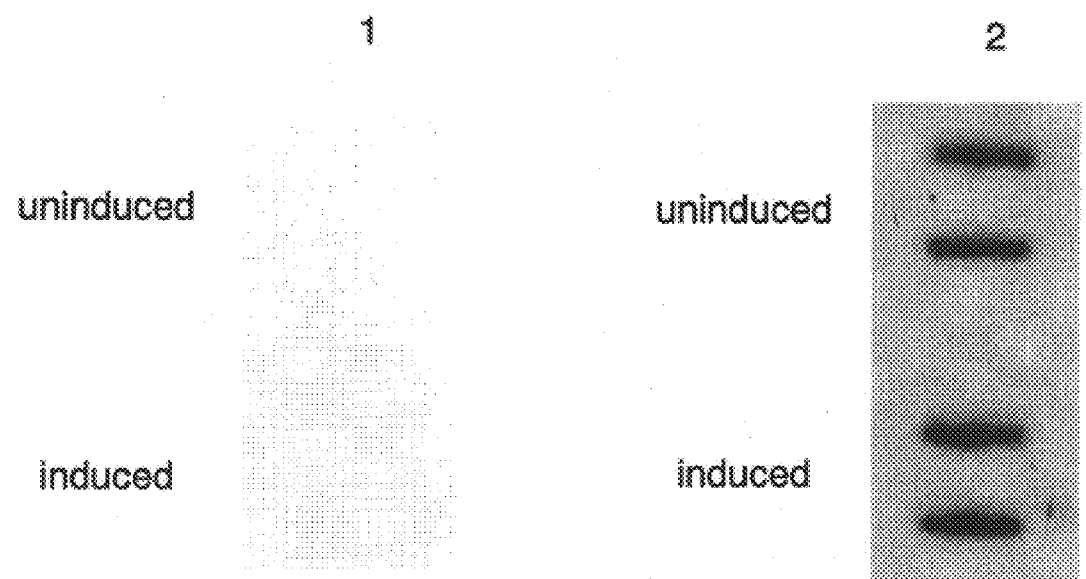

Uninoculated microcosms. At the 4 h period, when soil slurry samples were processed for total RNA, the heterotrophic cell count was determined to be 2.23 ( $0.15\times10^6$ cells/g for the microcosm without toluene and 2.07 ( $0.31\times 10^6$ cells/g for the toluene induced microcosm. TodC1 positive populations for the uninduced microcosms were 5.17( $1.0\times10^5$ cells/g and 4.00 ( $2.2\times10^5$ cells/g for the toluene-induced microcosms. Mass determinations of soil derived total RNA made by hybridization of $^{32}$P-labeled universal rRNA oligonucleotides agreed with determinations based on absorbance (260 nm) readings (data not shown). RNA extraction of uninoculated soil microcosms yielded 9.8 ng from toluene induced and 9.4 ng from uninduced soils. Because of the low RNA yield, a check of RNA integrety by visualization was not made. DD experiments with uninoculated microcosm derived RNA yielded several differential bands (FIG. 8). Upon cloning and sequencing these bands, clone 70.3–400 was found to be both unique and differentially expressed as determined by RNA slot blots (FIG. 9C-1). Probing slot blots with clone 70.3–325 revealed it to be a ribosomal subunit and allowed it to serve as an indicator of equal slot blot loading (FIG. 9C-2).

Differential display of uranium induced soil microcosms.

Isolation of differentially expressed PCR products

The effects of uranium was also studied in a more complex environment using an aquifer soil. RNA fingerprints from the differential display gel revealed a number of putative differentially expressed bands (FIG. 12). Rifampicin was also added to the soil, excised from the gel, reamplified, and resolved on a 1% low-melting agarose gel to verify that the bands had been isolated from the differential display gel (data not shown). been isolated from the differential display gel (data not shown). However, no decaying band patterns indicative of rifampicin transcriptional inhibition were observed.

Figure 13:
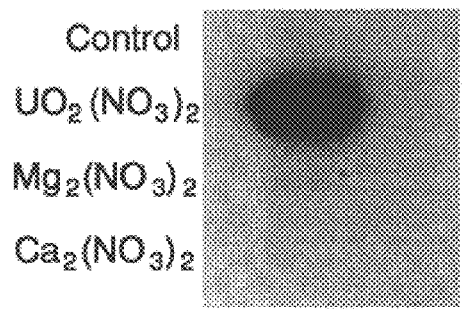

Verification of differential expression and sequence analysis. To verify differential expression, RNA slot blot analysis was accomplished using total RNA obtained from the control and uranium-induced soil microcosms. Of the four putative differentially expressed fragments isolated from the differential display, one band was confirmed to be differentially expressed (FIG. 13). The differential transcript corresponding to the original differential display gel was approximately 1200bp in length. Subsequently, clone 60.3–1200 was sequenced and compared to those sequences available on the Genbank Blast algorithm. Sequence analysis results showed no similarity to any of the sequences in the GenBank database. This was expected to some extent because the soil is highly uncharacterized.

Verification that differential expression is due to the uranyl ion. Control and uranyl nitrate induced microcosms were set up along with two additional negative control microcosms: 200 μM calcium nitrate and 200 μM magnesium nitrate. Conditions for this experiment were analogous to those conditions which had generated the differential band (clone 60.3–1200). Results from RNA slot blot analysis revealed negative hybridization to the three controls and positive hybridization in the slot which contained uranyl nitrate induced total RNA (FIG. 13).

EXAMPLE 12

Application of rifampicin to reduce false positives (Inventive). Prior to harvesting, cells were treated with the transcriptional inhibitor, rifampicin to help distinguish between those messages related to induction and other artifacts (rRNAs, tRNAs etc.). 1 ml of rifampicin (at a stock concentration of 20 mg/ml) was added to the flask containing the induced cells to give a final concentration of 200μg/ml. Following the addition of rifampicin, 15 ml aliquots were taken at the following time intervals: 5, 10, 20, 30, 40, and 60 min. Cells were harvested by centrifugation at 8,000 RPM for 5 min at 4° C. and immediately stored at −80° C. until ready for use.

EXAMPLE 13

Elution of differential display bands and PCR reamplification. Differential cDNA bands were detected by side-by-side comparison of induced versus uninduced PCR products on the autoradiogram. Gel bands were localized by overlaying the dried gel with the film. Bands were first softened by the addition of 5 μl of distilled water and then excised with a sterile razor blade. 500 μl of TE buffer was added to the gel slice and heated at 68° C. for at least 2 h. The excised fragments were re-amplified by using the same conditions as the first PCR run, except that the final concentration of dNTPs was changed to 200 μM. The re-amplification products were electrophoresed into 1% low melting agarose and products with the same molecular weight as the original DD bands were excised with a razor blade. TBE buffer (250 μl) was added to the gel slice and incubated at 65° C. for 10 min. Agarase (4 μl) was then added to the solution and incubated at 42° C. for 2 hrs after which the mix was then filtered using a Z-spin column (Gelman, Ann Arbor, Mich.). The solution was extracted with phenol/chloroform (1:1) and precipitated by the addition of ethanol.

EXAMPLE 14

Cloning of differential display derived PCR products. Cloning was done using a TA cloning kit following the manufacturer's protocols. 1 μl of the purified PCR product was used for the transformation. The white colonies were transferred to another plate containing 100 mg/ml of ampicillin and 40 μl of X-gal (0.1 g/5ml). Plasmid DNA was prepared by either the boiling method or alkali lysis method. Following isolation the crude DNA was resuspended in 20 μl of TE buffer, RNase treated at 37° C. for 30 minutes, extracted twice with 1:1 phenol/chloroform, precipitated and washed with 70% ethanol. The presence of inserts was checked by electrophoresis after restriction with EcoRI. The inserted cDNA was then eluted to 1% low melting agarose, excised and used as a template for probing.

End of Examples.

Verification of differential gene expression. Initially gel-purified re-amplification products were labeled by the random primer extension method using the manufacturer's protocol and used to probe RNA slot blots from induced and uninduced samples. This initial screening process was later eliminated. Subsequently, re-amplification products were cloned into the pCRII vector (Invitrogen), EcoRI restricted plasmid DNA was labeled by the random primer method and used as a probe to hybridize with slot blots from induced and uninduced samples obtained from pure culture and inoculated microcosm derived RNA.

Sequencing and Data search. Sequencing was done by an automated unit and the obtained sequences were compared with Genbank archives using the BLAST algorithm (Basic local alignment search tool, J. Mol. Biol., 15:403–10). Prior to computer analysis the automated readout was visually inspected for deletions. Both the BLASTN and BLASTX functions were used.

Verification of differential expression. For the optimization experiment using tod specific primers, toluene induction of P. putida F1 derived clone 410 a (FIG. 8-1) was verified to be differentially expressed by RNA slot blots (FIG. 9A). After sequencing and a GenBank search, both clones were found to be 100% homologous to TodC1.

Optimization of Differential Display for Prokaryotic RNA. Until recently the method of choice for the detection of differentially expressed genes has been subtractive hybridization. However, this technique requires a large amount of RNA, is very tedious, and, generally, is not reproducible. Two groups developed an alternative approach referred to as either DD or RAP-PCR that is better suited for screening multiple samples with lower quantities of RNA. While most attention has been paid to the application of differential display to eukaryotic systems, the technique may actually be better suited to prokaryotic RNA. On the basis of reassociation kinetics it is estimated that a typical mammalian cell has 360,000 mRNA molecules per cell with 20,000 to 30,000 different mRNAs species that range from 15 to 12,000 copies per species. In contrast, prokaryotes are estimated to have only 1,380 mRNA molecules per cell represented by 400 different mRNA species. Because the complexity of prokaryotic mRNAs is much less that that of eukaryotic mRNAs, it should theoretically be easier to obtain rare transcripts from prokaryotes by DD.

The differential display technique involves several steps: 1) Isolation of intact RNA from organisms; 2) Reverse transcription of total RNA using either an arbitrary primer or oligo dT primer (for eukaryotic systems) to generate cDNA; 3) PCR amplification using an arbitrary primer or an arbitrary primer paired with an oligo dT primer (for eukaryotic systems) to amplify the cDNA; 4) Separation and detection of the differential PCR products on sequencing gels; 5) re-amplification and cloning of the isolated PCR products; 6) Verification of the differential expression of the isolated gene fragment by northern blots, RNA slots blots, ribonuclease protection assay or RT-PCR, 7) Comparison of sequence similarity with known gene sequence databases permits the possible function of the gene to be inferred. The isolated gene fragment can be further used as a probe to locate and isolate the entire gene.

Initial attempts using a previously published prokaryotic RAP-PCR protocol yielded only rRNA fragments from putative differentially displayed bands (data not shown). The half-lives of several catabolic mRNAs including nah, tod and phe are seen to be greater than 10 min (unpublished data) as our difficulties could not be attributed to physiological degradation of messages alone. Therefore, parameters such as annealing temperature, primer size and concentration, magnesium and nucleotide concentration, and RNA template concentration were empirically examined to optimize the procedure for application to RNA derived from both prokaryotic pure cultures and soil communities.

Once parameters were optimized using specific tod primers, the procedure was modified for application to unknown sequences by using an arbitrary primer for the RT step and a general primer to the Shine-Dalgarno (SD) region in conjunction with the same arbitrary primer for the PCR step. The use of a SD primer herein is intended to prime the 5' region of a wide range of prokaryotes. An ideal SD primer would be advantageous in that it would allow preferential amplification at the 5' end of all cistrons within a polycistronic prokaryotic message. The SD region is characterized by a purine-rich region 5 to 6 bases from the start site. The primer used in this study includes the an ATG start codon at the 3' end with additional 5' bases based on a comparison of Pseudomonas and E. coli SD regions. Because of substitutions, albeit conservative, a simple primer based entirely on conserved sequences is infeasible. A degenerate SD primer incorporating equal molar amounts of G and A or inclusion of the altered 'P' base (6H,8H-3,4-dihydropyrimido[4,5-c][1,2]oxazin-7-one, 8-[(5 '-dimethoxytrityl-§-D-deoxyribofuranosyl),3'-[(2 -cyanoethyl)-(N,N-diisopropyl)] may result in a primer that would anneal to a greater number of SD regions in a greater number of organisms. The choice of a 5' SD primer, while generally biasing amplification toward mRNA sequences in a pool of prokaryotic RNA sequences may, however, ignore those messages that do not have SD regions. The use of two arbitrary primers for prokaryotic DD may thus be potentially advantageous.

Even when specific primers were used to specifically amplify the TodC1 gene approximately 70 other distinct bands, presumably ribosomal in origin, were also amplified. Since the primers were designed in such a way that specific annealing of the P. piltida rRNA to the 3' end of the primer was diminished, the observed amplification of rRNA is due to mismatch amplification. Theoretically, the annealing temperature will largely influence the differential display result; the higher the annealing temperature, the fewer the number of mispriming events. However, the current data shows that the annealing temperature did not have much influence on the total number of bands generated or the banding patterns. When the annealing temperature was increased from 30 to 50(C, only a slight band pattern change was observed (FIG. 4A). This may be explained by the fact that the PCR enhancers Triton-X 100 and DMSO were added to the PCR reaction mixture, which reportedly increases PCR efficiency and specificity. Alternatively it may be attributed to the template or the particular primer used.

The primer length also had a great influence on fingerprinting band patterns. Compared to fingerprints generated with 10 bp primers, more bands per lane were obtained by using 13 bp primers (FIG. 4B). This is most probably due to increased mis-priming with the longer primer. Based on experience, after the initial optimization work, the best results were obtained using an arbitrary 10 bp primer for the RT step and the SD14 (general) primer in conjunction with the same arbitrary primer for PCR.

Primer concentration also has great influence on the banding pattern. The best primer concentration was determined to be in the range of 0.2 to 2 $\mu$M. Above 20 $\mu$M, the non-specific priming increases, therefore, increasing the background (FIG. 3B). Too low a primer concentration decreases the band intensity and complexity. Nucleotide concentrations also play a very important role in the DD technique; above 200 $\mu$M, the incorporation rate of the radiolabeled dNTP is very low and the differential band intensity is also lowered. Lower than 2 $\mu$M, all bands are not amplified most probably due to depletion of dNTPs (FIG. 3A, lane 5).

Thus per the invention, the differential display (DD) technique, widely used almost exclusively for eukaryotic gene discovery, is optimized to detect differential mRNA transcription from both pure culture and soil derived bacterial RNA. A model system using toluene induction of TodC1 in Pseudomonas putida F1 is used to optimize the procedure. Primer concentration, primer length, annealing temperature, template, dNTP and MgC12 concentration are varied to optimize the amplification of a TodC1 fragment on sequencing gels. Once optimized, an arbitrary primer for the RT step in conjunction with the same arbitrary primer and a Shine-Dalgarno (SD) primer for the PCR reaction is used to detect tod transcription in P. putida F1 and a new salicylate inducible naphthalene dioxygenase in P. putida JS 150. To help reduce the number of false positives, rifampicin is added to pure cultures and microcosms to allow discrimination between PCR products derived from ribosomal subunits and mRNAs. The method is then applied to detect mRNA induction in both inoculated and uninoculated toluene, cadmium and uranium induced soil microcosms. Of a number of putative differentially expressed partial gene sequences obtained from the uninoculated microcosms, several have been verified to be differentially expressed. The invention thus provides a process for discovery and acquisition of novel genes from environmental microbial communities that avoids the traditional steps and inherent bias due to the culturing of environmental isolates.

In a preferred embodiment, the inventive method extracts RNA from a soil sample and isolates one or more expressed genes therefrom by DD, using an arbitrary primer for the RT reaction and the same arbitrary primer (eg.,on an equi-molar basis) with a Shine-Dalgarno (SD) (general) primer for PCR.

What is claimed is:

1. A method for identifying at least one gene in a sample comprising,
   a) adding a contaminant to the sample to perturb microbial organisms in the sample and cause at least one gene therein to be expressed,
   b) extracting RNA from said sample without prior cell separation and
   c) isolating at least one type of expressed gene from said sample by differential display (DD) using a reverse transcriptase (RT) step and a polymerase chain reaction (PCR) step wherein an arbitrary primer is used for said RT step, and the same arbitrary primer is used with a Shine-Dalgarno (SD) primer for said PCR step.

2. The method of claim 1 wherein said RNA is extracted by lysing the cells in situ and separating nucleic acids from said sample.

3. The method of claim 1 wherein said RNA is extracted from said sample before and after the perturbing step for comparative measurements.

4. The method of claim 1 wherein the adding, extracting and isolating steps are carried out without prior culturing of said organisms.

5. The method of claim 1 wherein said sample is selected from the group consisting of a culture, a pure culture and soil.

6. The method of claim 1 wherein said contaminant is selected from the group consisting of hydrocarbons, metals and a combination thereof.

7. The method of claim 1 wherein said contaminant is selected from the group consisting of hydrocarbon fuels, oils and toluene.

* * * * *

SEQUENCE LISTING (1) GENERAL INFORMATION:

(iii) NUMBER OF SEQUENCES:1

(2) INFORMATION FOR SEQ ID NO: 1:

(i) SEQUENCE CHARACTERISTICS:
      (A) LENGTH: 14 bases
      (B) TYPE: nucleic acid
      (C) STRANDEDNESS: single
      (D) TOPOLOGY: linear (ii) MOLECULE TYPE: synthetic oligonucleotides (iii) HYPOTHETICAL: no (iv) ANTI-SENSE: no (vi) ORIGINAL SOURCE: n/a (vii) IMMEDIATE SOURCE: n/a (x) PUBLICATION INFORMATION:
      (A) AUTHORS: Fleming, James T. Yao, Wen-Hsiang  Sayler, Gary S.
      (B) TITLE: Optimization of differential display of prokaryotic
          mRNA: Application to pure culture and soil microorganisms
      (C) JOURNAL: Applied and Environmental Microbiology
      (D) VOLUME: 64
      (E) ISSUE: 10
      (F) PAGES: 3698-3706
      (G) DATE: October 1998

(xi) SEQUENCE DESCRIPTION: SEQ  ID  NO: 1:

GGGGAACGAC GATG                                                            14